(12) United States Patent
Spilka et al.

(10) Patent No.: US 12,185,934 B2
(45) Date of Patent: Jan. 7, 2025

(54) ADAPTER INSERTER AND DOCKING STATION

(71) Applicant: Biomet Manufacturing, LLC, Warsaw, IN (US)

(72) Inventors: David G. Spilka, Phoenix, AZ (US); Kevin N. Baird, Scottsdale, AZ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 614 days.

(21) Appl. No.: 17/598,625

(22) PCT Filed: Mar. 30, 2020

(86) PCT No.: PCT/US2020/025700
§ 371 (c)(1),
(2) Date: Sep. 27, 2021

(87) PCT Pub. No.: WO2020/210073
PCT Pub. Date: Oct. 15, 2020

(65) Prior Publication Data
US 2022/0160346 A1 May 26, 2022

Related U.S. Application Data

(60) Provisional application No. 62/831,458, filed on Apr. 9, 2019.

(51) Int. Cl.
*A61B 17/04* (2006.01)
*A61B 17/00* (2006.01)
*A61F 2/08* (2006.01)

(52) U.S. Cl.
CPC ........ *A61B 17/0401* (2013.01); *A61F 2/0811* (2013.01); *A61B 2017/00367* (2013.01);
(Continued)

(58) Field of Classification Search
CPC ...... A61B 17/0401; A61B 2017/00367; A61B 2017/00469; A61B 2017/00477;
(Continued)

(56) References Cited

U.S. PATENT DOCUMENTS 8,858,565 B1 * 10/2014 Hoof .................. A61B 17/8888
606/104
2011/0022748 A1   1/2011 Edwards et al.
(Continued)

FOREIGN PATENT DOCUMENTS

WO   WO-2020210073 A1   10/2020

OTHER PUBLICATIONS

"International Application Serial No. PCT/US2020/025700, International Search Report mailed Jun. 29, 2020", 6 pgs.
"International Application Serial No. PCT/US2020/025700, Written Opinion mailed Jun. 29, 2020", 9 pgs.
(Continued)

*Primary Examiner* — Tan-Uyen T Ho
*Assistant Examiner* — Osama Nemer
(74) *Attorney, Agent, or Firm* — SCHWEGMAN LUNDBERG & WOESSNER, P.A.

(57) ABSTRACT

Disclosed is a system for inserting an adapter including a docking station and an adapter inserter. The docking station can include a handle block, a push assembly, and a linkage connecting knob push handle to an engagement tube pull block. The engagement tube pull block can extend from the linkage through a portion of the handle block. The adapter inserter can include a handle body, an engagement assembly, and a clamp. The handle body can be sized to fit in a first recess defined by the handle block body. The engagement assembly can extend from a second end of the handle body and can be configured to engage the adapter at a tip of the engagement assembly. The clamp can be located within and proximate a second end of the handle body so as to engage a portion of the engagement assembly.

19 Claims, 7 Drawing Sheets

(52) U.S. Cl.
CPC ............... *A61B 2017/00469* (2013.01); *A61B 2017/00477* (2013.01); *A61B 2017/0409* (2013.01); *A61B 2017/0464* (2013.01); *A61F 2002/0858* (2013.01)

(58) Field of Classification Search
CPC .... A61B 2017/0409; A61B 2017/0464; A61B 90/50; A61B 17/8888; A61B 50/20; A61B 2017/00424; A61B 2017/00429; A61B 2017/0084; A61B 2560/0456; A61B 2090/034; A61B 2090/0813; A61B 17/0483; A61B 17/3468; A61B 17/10; A61B 17/128; A61B 17/1285; A61B 17/8894; A61B 34/70; A61F 2/0811; A61F 2002/0858; A61F 2/4603
See application file for complete search history.

(56) References Cited

U.S. PATENT DOCUMENTS

| | | | |
|---|---|---|---|
| 2013/0325063 | A1 | 12/2013 | Norton et al. |
| 2014/0364891 | A1 | 12/2014 | Mendius et al. |
| 2016/0367357 | A1* | 12/2016 | Dougherty ......... A61B 17/0483 |
| 2018/0168746 | A1* | 6/2018 | Swayze .............. A61B 17/3423 |
| 2018/0271526 | A1* | 9/2018 | Zammataro ............ A61B 17/10 |
| 2018/0353179 | A1* | 12/2018 | Shelton, IV ..... A61B 17/07207 |
| 2019/0216554 | A1* | 7/2019 | Kapadia ................. A61B 46/10 |

OTHER PUBLICATIONS

"International Application Serial No. PCT US2020 025700, International Preliminary Report on Patentability mailed Oct. 21, 2021", 11 pgs.

* cited by examiner

ADAPTER INSERTER AND DOCKING STATION

CLAIM OF PRIORITY

This application is a U.S. National Stage Application under 35 U.S.C. 371 from International Application Serial No. PCT/US2020/025700, filed on Mar. 30, 2020, and published as WO 2020/210073 A1 on Oct. 15, 2020, which claims the benefit of U.S. Provisional Patent Application Ser. No. 62/831,458, filed on Apr. 9, 2019, the benefit of priority of each of which is claimed hereby, and each of which is incorporated by reference herein in its entirety.

FIELD OF THE DISCLOSURE

The present disclosure relates to adapter inserters and docking stations. Specifically, the present disclosure relates to docking stations for use with adapter inserters and use thereof.

BACKGROUND

During surgeries ligaments, tendons, and sutures can be attached to bone or other structures within a patient. To attach the ligaments, tendons, and sutures an adapter can be implanted or otherwise attached to the bone or other structures within the patient. To implant the adapter, the adapter can first be attached to an adapter inserter. The adapter inserter can then be used by a surgeon to implant the adapter.

SUMMARY

To better illustrate the systems and methods disclosed herein, a non-limiting list of examples is provided here:

Example 1 is a docking station for an adapter inserter, the docking station comprising: a handle block having a first surface that defines a first recess sized to receive a portion of the adapter inserter and a second surface that defines a channel; and a push assembly comprising: a knob push handle, an engagement tube pull block configured to contact a portion of an engagement tube of the adapter inserter, and a linkage shaft connecting the knob push handle to the engagement tube block, the linkage shaft slidably located in the channel, the engagement tube pull block extending from the linkage through a portion of the handle block such that a portion of the engagement tube pull block is located in the recess.

In Example 2, the subject matter of Example 1 optionally includes a first handle retainer arm located proximate a first end of the recess and extending from the handle block above the first surface of the handle block; and a handle retainer push handle operatively connected to the first handle retainer arm, the first handle retainer arm and the handle retainer push handle movable from a locked position to an unlocked position.

In Example 3, the subject matter of Example 2 optionally includes a second handle retainer arm, the first handle retainer arm and the second handle retainer arm located on opposite sides of a slot defined by the handle block.

In Example 4, the subject matter of any one or more of Examples 2-3 optionally include a locking block located proximate a first end of the handle block, the locking block operatively connected to the handle retainer push handle and translatable normal to the first handle retainer arm.

In Example 5, the subject matter of Example 4 optionally includes a locking block shaft configured to cause the locking block to move upon movement of the handle retainer push handle.

In Example 6, the subject matter of any one or more of Examples 2-5 optionally include wherein the handle retainer push handle and the first handle retainer arm are spring loaded.

In Example 7, the subject matter of any one or more of Examples 1-6 optionally include a lock push block projecting into the recess and configured to disengage a clamp of the adapter inserter.

In Example 8, the subject matter of any one or more of Examples 1-7 optionally include a knob push block located proximate the knob push handle, the knob push block defining an indentation sized to receive a portion of a rotatable knob of the adapter inserter.

In Example 9, the subject matter of any one or more of Examples 1-8 optionally include a base plate connected to the second surface of the handle block.

Example 10 is an adapter inserter for use with a docking station, the adapter inserter comprising: a handle body having a first end and a second end, the handle body defining a through hole extending from the first end to the second end; an engagement assembly extending from the second end of the handle body and configured to engage an adapter at a tip of the engagement assembly; and a clamp located within and proximate the second end of the handle body, the clamp arranged to engage a portion of the engagement assembly, the clamp having a contact surface arranged to engage a lock push block of the docking station.

In Example 11, the subject matter of Example 10 optionally includes where the engagement assembly comprises: an engagement tube extending from the second end of the handle body; and an engagement shaft located within the engagement tube and extending from the second end of the handle body, wherein the clamp is arranged to contact the engagement tube.

In Example 12, the subject matter of Example 11 optionally includes wherein the engagement assembly comprises a rotatable knob connected to the engagement shaft such that rotation of the rotatable knob in a first direction causes the engagement shaft to travel in a first direction and rotation of the rotatable knob in a second direction causes the engagement shaft to travel in a second direction.

In Example 13, the subject matter of any one or more of Examples 10-12 optionally include wherein the engagement shaft includes a protrusion sized to fit a detent of the adapter.

In Example 14, the subject matter of Example 13 optionally includes a pull knob located proximate the first end of the handle body, the pull knob operatively connected to the engagement assembly such that a movement of the pull knob causes the protrusion to recede from the detent of the adapter.

In Example 15, the subject matter of any one or more of Examples 10-14 optionally include wherein the clamp comprises clamp teeth and the engagement tube comprises engagement teeth, the clamp teeth arranged to engage the engagement teeth.

In Example 16, the subject matter of any one or more of Examples 10-15 optionally include wherein the handle body defines at least one protrusion located proximate the second end of the handle body, the at least one protrusion sized to engage a handle retainer of the docking station.

Example 17 is a system for inserting an adapter, the system comprising: a docking station comprising: a handle block that defines a channel and a first recess, a lock push block connected to the handle block and protruding into the first recess, and a push assembly comprising a knob push handle, an engagement tube pull block, and a linkage connecting the knob push handle to the engagement tube pull block, the linkage slideably located in the channel, the engagement tube pull block extending from the linkage through a portion of the handle bock into the recess; and an adapter inserter comprising: a handle body having a first end and a second end, the handle body sized to fit in a first recess defined by the handle block and defining a through hole extending from the first end to the second end, an engagement assembly extending from the second end of the handle body and configured to engage the adapter at a tip of the engagement assembly, and a clamp located within and proximate the second end of the handle body, the clamp arranged to engage a portion of the engagement assembly, the clamp having a contact surface arranged to engage the lock push block of the docking station.

In Example 18, the subject matter of Example 17 optionally includes wherein the engagement assembly comprises: an engagement tube extending from the second end of the handle body; and an engagement shaft located within the engagement tube and extending from the second end of the handle body, wherein the clamp is arranged to contact the engagement tube.

In Example 19, the subject matter of any one or more of Examples 17-18 optionally include wherein the clamp comprises clamp teeth and the engagement tube comprises engagement teeth, the clamp teeth arranged to engage the engagement teeth.

In Example 20, the subject matter of any one or more of Examples 17-19 optionally include wherein the docking station further comprises: a handle retainer arm located proximate a first end of the first recess and extending from the handle block, and a handle retainer push handle operatively connected to the handle retainer arm, the handle retainer arm and the handle retainer push handle movable from a locked position to an unlocked position; and the adapter inserter further comprises: at least one protrusion extending from the handle body and located proximate the second end of the handle body, the at least one protrusion sized to engage the first handle retainer of the docking station.

In Example 21, the adapter inserters, docking stations, or methods of any one of or any combination of Examples 1-20 are optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

During various surgical procedures, anchors or other implantable fixtures can be inserted into a patient. For example, during a knee surgery, an anchor, also referred to as an adapter, can be implanted into the tibia or femur so that ligaments, tendons, or sutures can be affixed to bone. To implant the adapter, an adapter insertion tool can be used.

Disclosed herein is a reusable adapter inserter and a docking station for using the same. The reusable adapter inserter can be placed in an autoclave for cleaning between uses. The adapter inserter can include an engagement assembly extending from a second end of a handle body of the adapter inserter. The engagement assembly can be configured to engage an adapter at a tip of the engagement assembly. The engagement of the adapter at the tip of the engagement assembly can allow for the adapter to be releasably connected to the adapter inserter such that when the adapter is implanted, it can be released from the tip.

To install the adapter to the adapter inserter, the adapter inserter can be placed in the docking station and a knob push handle of the docking station can be manipulated such that a pull knob of the adapter inserter is repositioned. Repositioning of the pull knob can cause a portion of the tip of the engagement assembly to be exposed. The adapter can then be placed on the exposed tip. Upon placing the adapter onto the tip, the knob push handle of the docketing station can be released and the engagement assembly can secure the adapter to the adapter inserter.

Upon implanting the adapter, a rotatable knob of the adapter inserter can be rotated in a first direction. Rotation of the rotatable knob can cause the portion of the tip to which the adapter is attached to become exposed, or otherwise released from the adapter, thereby releasing the adapter from the adapter inserter. Rotation of the rotatable knob can also cause an engagement shaft of the engagement assembly to rotate. Rotation of the engagement shaft can cause the adapter to expand, thereby causing the adapter to become affixed to bone.

Figure 1:
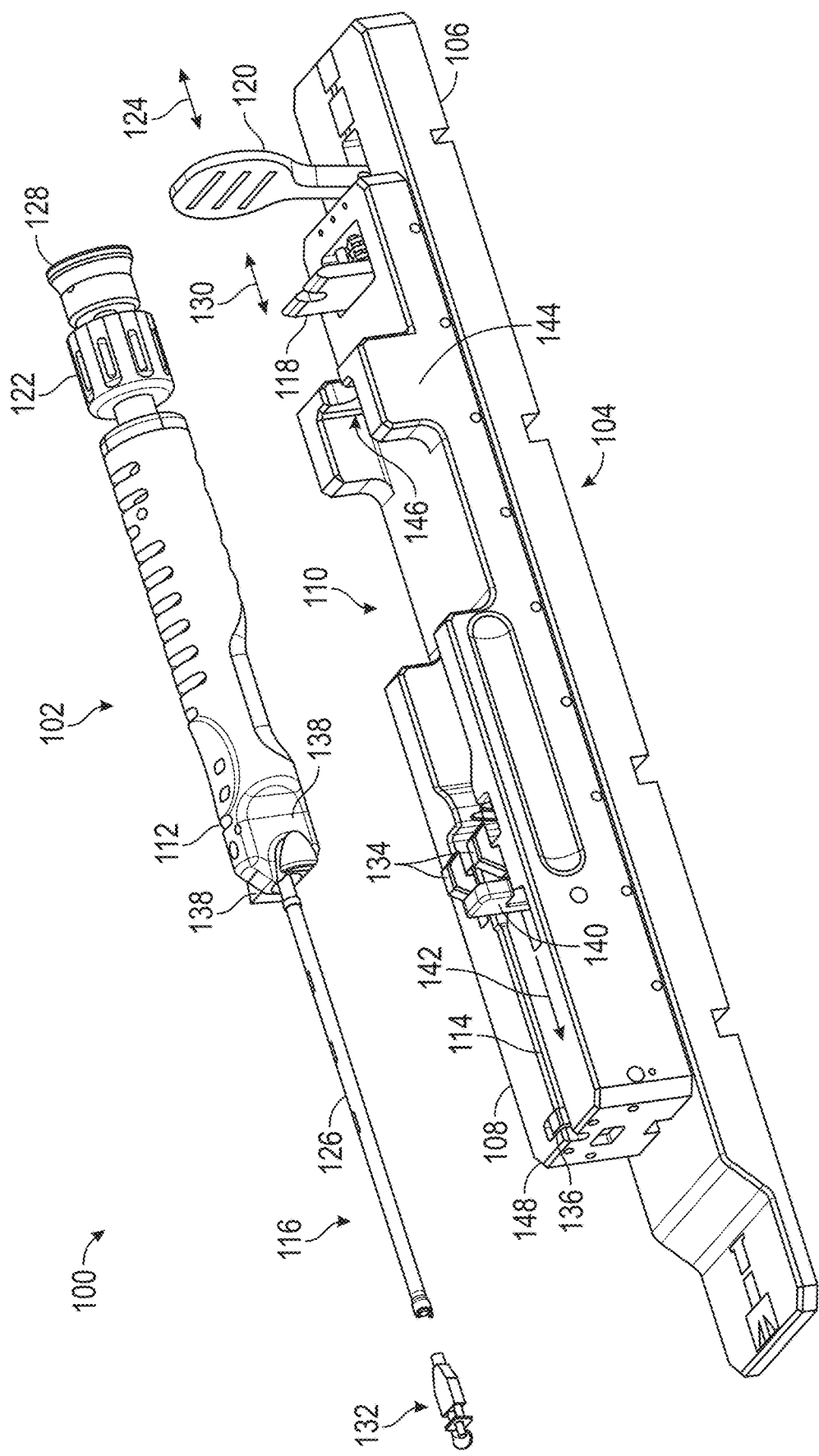
FIG. 1 shows a system for inserting an adapter in accordance with at least one example of the present disclosure.
Figure 2:
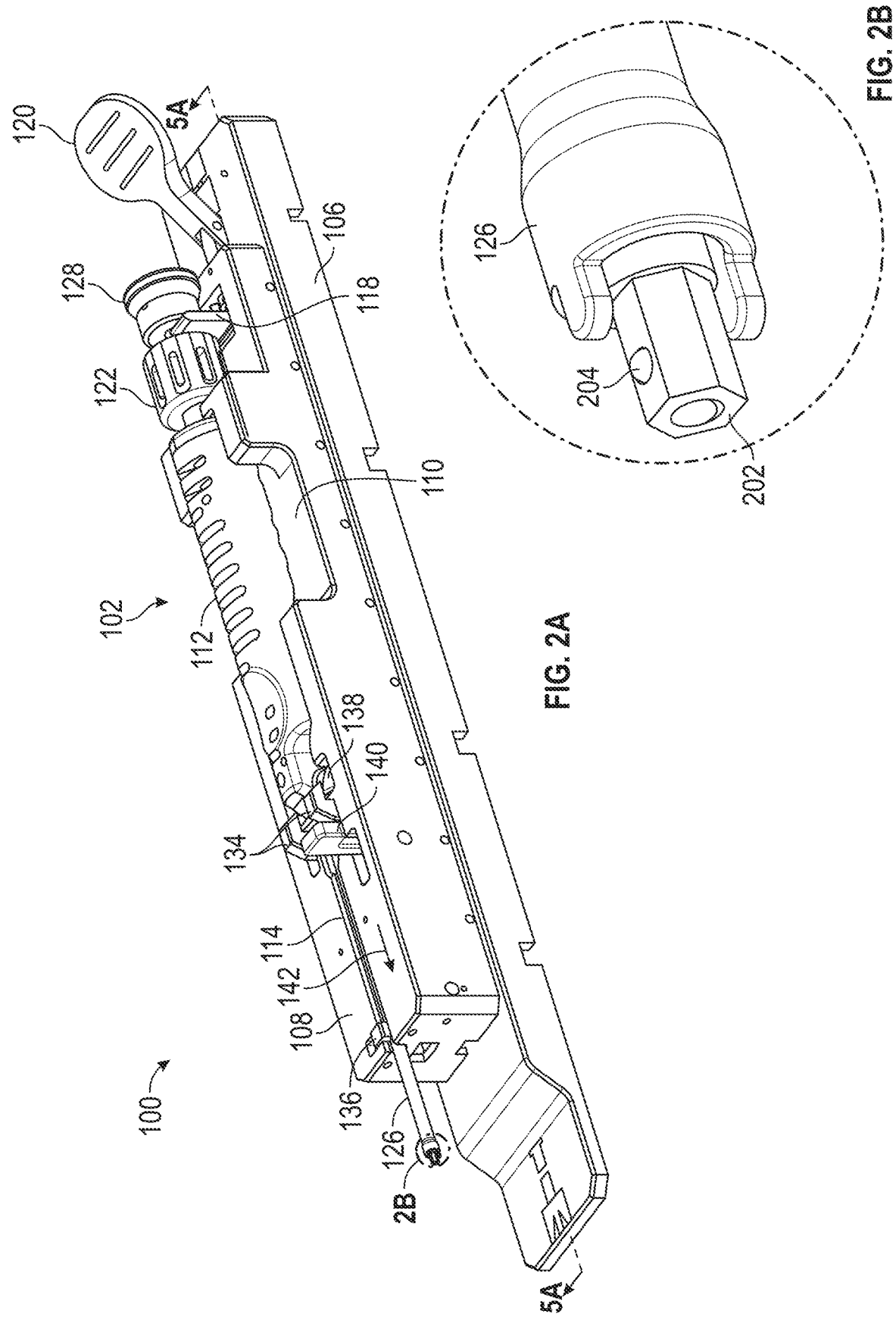
FIG. 2A shows a system for inserting an adapter in accordance with at least one example of the present disclosure.
FIG. 2B shows a detail of the system for inserting an adapter shown in FIG. 2A in accordance with at least one example of the present disclosure.

Turning now to the figures, FIGS. 1, 2A, and 2B show a system 100 for inserting an adapter in accordance with at least one example of the present disclosure. As shown in FIGS. 1 and 2A, system 100 can include an adapter inserter 102 and a docking station 104. Docking station 104 can include a base plate 106 and a handle block 108. Handle block 108 can define a recess 110 into which a handle body 112 of adapter inserter 102 can fit. Handle block 108 can also define a slot 114 into which an engagement assembly 116 can fit. Docking station 104 can also include a knob push block 118 that can be operatively connected to a knob push handle 120 as disclosed herein. Knob push block 118 can engage adaptor inserter 102 by being located in between a rotatable knob 122 and knob push handle 120. As disclosed herein, movement of knob push handle 120 as indicated by arrow 124 from a first or proximal position as shown in FIG. 1 to a second or distal position as shown in FIG. 2A can cause an engagement tube 126 to translate and expose an engagement shaft 202 as shown in FIG. 2B. Movement of engagement tube 126 can be caused by movement of knob push block 118 which can cause movement of a pull knob 128 as indicated by arrow 130. Engagement shaft 202 can include a protrusion 204 that can engage an adapter 132 to secure adapter 132 to engagement shaft 202.

Docking station 104 can also include one or more handle retainers 134 and a locking block 136. When adapter inserter 102 is docked with docking station 104 handle retainers 134 can engage one or more protrusions 138 of adapter inserter 102. In addition, locking block 136 can engage engagement tube 126 so as to secure engagement tube 126 at least partially within slot 114. A handle retainer push handle 140 can be operatively connected to handle retainers 134 and locking block 136 such that movement of handle retainer push handle 140 as indicated by arrow 142 can cause handle retainers 134 and locking block 136 to disengage contact with protrusions 138 and engagement tube 126 so that adapter inserter 102 can be removed from docking station 104 as disclosed herein.

Use of handle retainers 134 and locking block 136 can allow adapter inserter 102 to be securely docked with docking station 104 so as to secure adapter inserter 102 in a fixed position for connecting adapter 132 to adapter inserter 102. Securing adapter inserter 102 in a fixed position can assist surgeons or other operating room personnel with handling adapters that may be small and adapter inserters that may be wet and slippery. Docking station 104 can be secured to a table, cart, or other fixture within an operating room. By securing docking station 104 to a table, cart, or other fixture within the operating room, the person attaching adapter 132 to adapter inserter 102 can manipulate handle retainer push handle 140 with one hand and place handle body 112 into recess 110 with the other. Once adapter inserter 102 is docked with docking station 104 the person attaching adapter 132 to adapter inserter 102 can manipulate knob push handle 120 with one hand and place adapter 132 onto engagement shaft 202 with the other.

As disclosed herein, to install adapter inserter 102 onto docking station 104, rotatable knob 122 can be fully unthreaded or loosened. Stated another way, rotatable knob 122 can be located at its farthest distance of travel away from handle body 112. Otherwise the adapter inserter 102 may not fit into recess 110 because rotatable knob 122 can be obstructed by a rear portion 144 of handle block 108, which can include an indentation 146 to receive a portion of rotatable knob 122.

Once adapter 132 has been attached to engagement shaft 202, adapter inserter 102 and adapter 132 can be placed into an autoclave for sterilization. Adapter 132 can also be placed onto engagement shaft 202 after adapter inserter 102 is sterilized in the autoclave. In addition, docking station 104 can also be placed in the autoclave for sterilization. Adapter inserter 102 can be docked to docking station 104 when placed in the autoclave so that docking station 104 can also be sterilized along with adapter inserter 102 and adapter 132.

Figure 3:
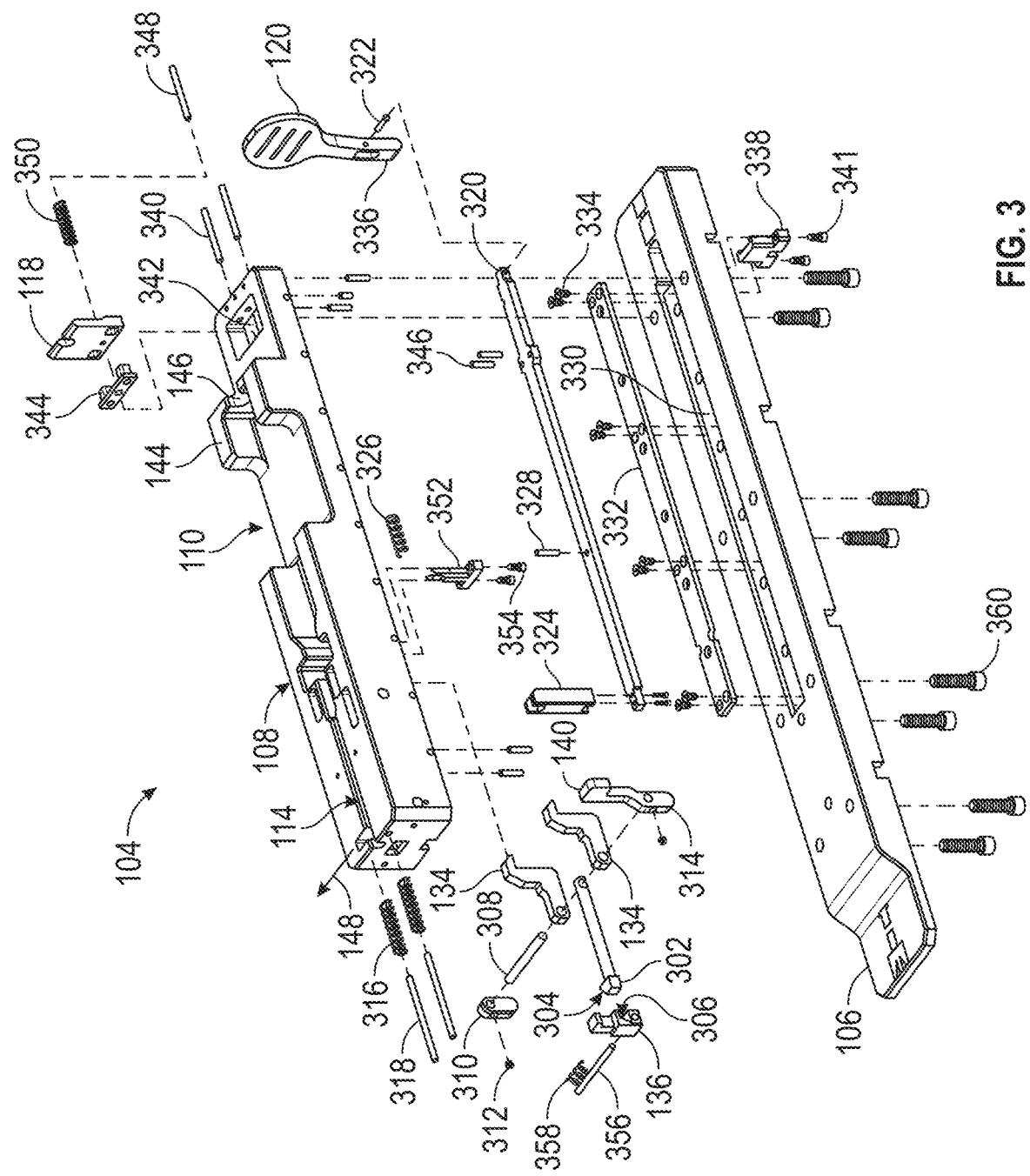
FIG. 3 shows a docking station in accordance with at least one example of the present disclosure.

FIG. 3 shows docking station 104 in accordance with at least one example of the present disclosure. More specifically, FIG. 3 shows an exploded assembly of docking station 104. As shown in FIG. 3, docking station 104 can further include a locking block shaft 302. Locking block shaft 302 can include an angled surface 304 that can contact an angled surface 306 of locking block 136. Locking block shaft 302 can be connected to handle retainer push handle 140 via a shaft 308. Shaft 308 can also connect handle retainers 134 to handle retainer push handle 140. A handle retainer push cam 310 can be connected to shaft 308 via a set screw 312 or other suitable fastening element. As shown in FIG. 3, handle retainer push handle 140 can include a cam portion 314.

When handle retainer push handle 140 is pushed from a first or proximal position to a second or distal position as indicated by arrow 142, cam portion 314 and handle retainer push cam 310 can contact an interior surface 502 (See FIG. 5B) and cause shaft 308, locking block shaft 302, and handle retainers 134 to translate in a direction as indicated by arrow 142. The movement of locking block shaft 302 can cause angled surface 304 to contact angled surface 306, which can in turn cause locking block 136 to translate away from slot 114 as indicated by arrow 148 along a shaft 356. The translation of handle retainers 134 and locking block 136 can allow protrusions 138 of handle body 112 and engagement tube 126 to be secured within handle block 108 so that engagement shaft 202 can be exposed via manipulation of knob push handle 120 as disclosed herein. A spring 358 can be used to bias locking block 136 into a locked position or in a direction opposite arrow 148.

Handle retainer push handle 140, and by extension handle retainers 134, can be biased to a locked position via springs 316. Springs 316 can be held in place with pins 318 or other suitable connecting members.

As shown in FIG. 3, a linkage shaft 320 can be connected to knob push handle 120 via a pin 322. An engagement tube pull block 324 can also be connected to linkage shaft 320. As a result, manipulation of knob push handle 120 as indicate by arrow 124 can cause engagement tube pull block 324 to translate in the same direction of knob push handle 120. As disclosed herein with respect to at least FIGS. 5A and 5B, movement of engagement tube pull block 324 toward a rear portion of handle block 108 can cause engagement tube 126 to move in the same direction of engagement tube pull block 324 so as to expose engagement shaft 202 and protrusion 204.

Linkage shaft 320 can be biased into a first position by a spring 326 that can press against handle block 108 and a pin 328 that can be connected to linkage shaft 320. The biasing of linkage shaft 320 can result in engagement tube pull block 324 being in a forward position so that adapter inserter 102 can be docked with docking station 104 without the user having to manipulate knob push handle 120. As a result, the user can use one hand to manipulate handle retainer push handle 140 and his or her other hand to position adapter inserter 102 appropriately to dock it with docking station 104.

Base plate 106 can define a channel 330. A linkage slide plate 332 can be secured to base plate 106 via one or more screws 334. Linkage slide plate 332 can provide a bearing surface for linkage shaft 320 to slide upon. Linkage slide plate 332 can be made of a polymer, metal, or ceramic that has a low coefficient of friction. In addition, linkage slide plate 332 can be changed upon showing signs of wear. As a result, both base plate 106 and linkage shaft 320 can have a higher service life since linkage slide plate 332 can provide for reduced friction.

Knob push handle 120 can include a cam portion 336. Cam portion 336 can press against base insert 338. That can be attached to base plate 106 via screws 341. Base insert 338 can be manufactured from a metal, polymer, or ceramic that has a low coefficient of friction so as to minimize wear of cam portion 336. Just as with linkage slide plate 332, base insert 338 can be replaced upon showing signs of excess wear.

Just as engagement tube pull block 324 translates with movement of knob push handle 120, knob push block 118 can also be engaged by linkage shaft 320 so as to move in the same direction as engagement tube pull block 324 with movement of knob push handle 120. As shown in FIG. 3, pins 340 can pass through a recess 342 defined by handle block 108. A knob push block bushing 344 can define one or more holes that pins 340 can pass through and ride upon. Knob push block bushing 344 can be made of a polymer, metal, or ceramic with a low coefficient of friction so as to minimize wear of pins 340. Knob push block bushing 344 can be replaced upon showing signs of wear without having to replace knob push block 118.

Pins 346 can be connected to linkage shaft 320 and contact knob push block bushing 344. As a result, when linkage shaft 320 moves rearward, pins 346 can cause knob push block 118 to move rearward as well. A pin 348 can pass through a spring 350 as well as knob push block 118 and knob push block bushing 344. Spring 350 can bias knob push block 118 and knob push block bushing 344 toward the front of handle block 108. As a result, spring 350 can act in concert with spring 326 to bias engagement tube pull block 324 and linkage shaft 320 towards the front of handle block 108.

Docking station 104 can also include a lock push block 352 that can be attached to handle block 108 via screws 354. As shown and described in FIGS. 5A and 5B, lock push block 352 can pass through a bottom portion of handle block 108 and into recess 110. When adapter inserter 102 is installed in docking station lock push block 352 can disengage a lock 402 to allow engagement tube 126 to translate about engagement shaft 202.

Base plate 106 and handle block 108, as well as the other components of docking station 104 can be manufactured from metals, polymers, ceramics, or any combination thereof. In addition, the various components of docking station 104 can be manufactured using injection molding, machining of billet materials, stamping, forge, etc. The selection of the materials as well as the method used to manufacture each part can be determined using a variety of factors such as wearability, ease of manufacturing, and interaction with other parts. For example, handle block 108 can be manufactured by injection molding or machining a polymer. Use of a polymer can minimize wear on the adapter inserter 102 due to contact handle block 108. Base plate 106 can be machined from a piece of aluminum or other suitable metal and bolted to handle block 108 via bolts 360. The metal base plate can allow for increased rigidity of docking station 104 and provide a strong material in which to use to bolt, clamp, or otherwise attach docking station 104 to a structure in an operating room.

Figure 4:
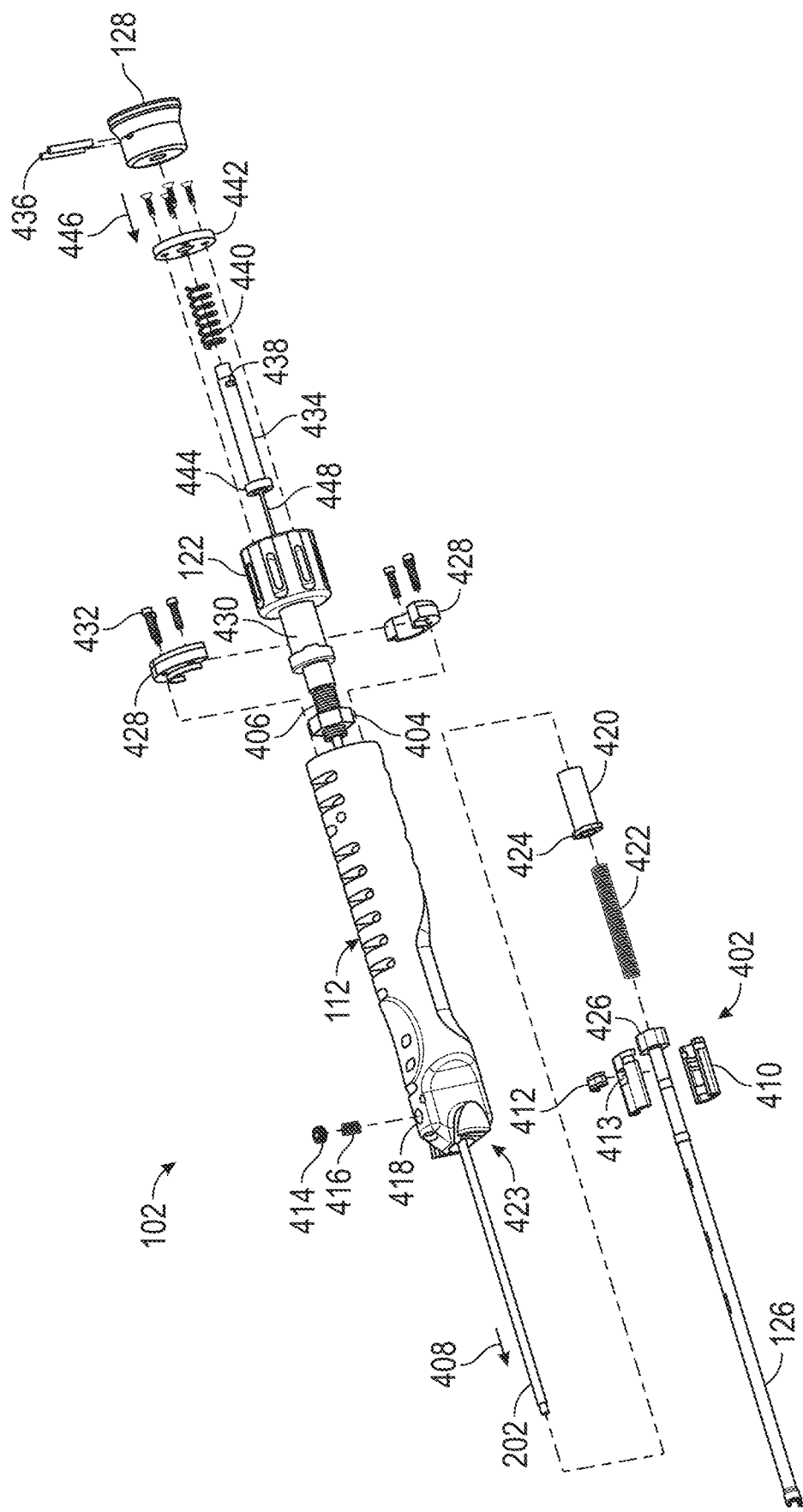
FIG. 4 shows an adapter inserter in accordance with at least one example of the present disclosure.

FIG. 4 shows adapter inserter 102 in accordance with at least one example of the present disclosure. More specifically, FIG. 4 shows an exploded assembly of adapter inserter 102. As shown in FIG. 4, engagement shaft 202 can pass through handle body 112 and be connected to rotatable knob 122. A nut 404 can operate in conjunction with a threaded portion 406 of rotatable knob 122. Once adapter 132 is implanted into a patient, rotatable knob 122 can be rotated in a first direction. Rotation of rotatable knob 122 in the first direction can cause engagement shaft 202 to translate as indicated by arrow 408. The translation of engagement shaft 202 can cause the tip of engagement shaft 202 to protrude from engagement tube 126, which in turn can cause adapter 132 to detach from engagement tube 126 or engagement shaft 202. Adapter 132 can also disengage from shaft 202 when inner shaft 448 is retracted by manipulating pull knob 128.

Adapter inserter 102 can include lock 402. Lock 402 can include a clamp retainer 410. Clamp retainer 410 can encircle a portion of engagement tube 126 and can define a hole 413. A clamp 412 can translate within hole 413 as shown and described with respect FIGS. 5A and 5B. A set screw 414 and a spring 416 can be used to retain clamp 412 in a hole 418 defined by handle body 112. Set screw 414 and spring 416 can be used to adjust a retention force exerted by clamp 412.

A bushing 420 and spring 422 can be located within handle body 112. Bushing 420 can be inserted into handle body 112 proximate a first end 423 and provide a bearing surface for engagement shaft 202 to articulate upon. Bushing 420 can also include a flange 424 that spring 422 can rest upon. Spring 422 can also press against a flange 426 of engagement tube 126 to bias engagement tube 126 to a position that covers protrusion 204 of engagement shaft 202.

Rotatable knob 122 can be secured to handle body 112 via a handle end cover 428. Handle end cover 428 can encircle a portion 430 of rotatable knob 122 and can be secured to handle body via one or more screws 432. Handle end cover 428 can also act as a bushing to facilitate rotation of rotatable knob 122.

Pull knob 128 can be connected to a spring shaft 434 via pins 436 that pass through pull knob 128 and grip spring shaft 434 via indentions 438. A spring 440 can be located on spring shaft 434 and apply force on a knob cover 442 and a flange 444 of spring shaft 434. Spring 440 can bias pull knob 128 in a direction as indicated by arrow 446. As a result, an inner shaft 448, which is connected to spring shaft 434, can be biased towards the tip of engagement shaft 202. Inner shaft 448 can pass through engagement shaft 202 and contact protrusion 204, which can be a spring-loaded detent. Once adapter 132 is implanted in the patient, the user can manipulate pull knob 128 in a direction opposite arrow 446, which can cause the spring-loaded detent to disengage adapter 132.

Figure 5A:
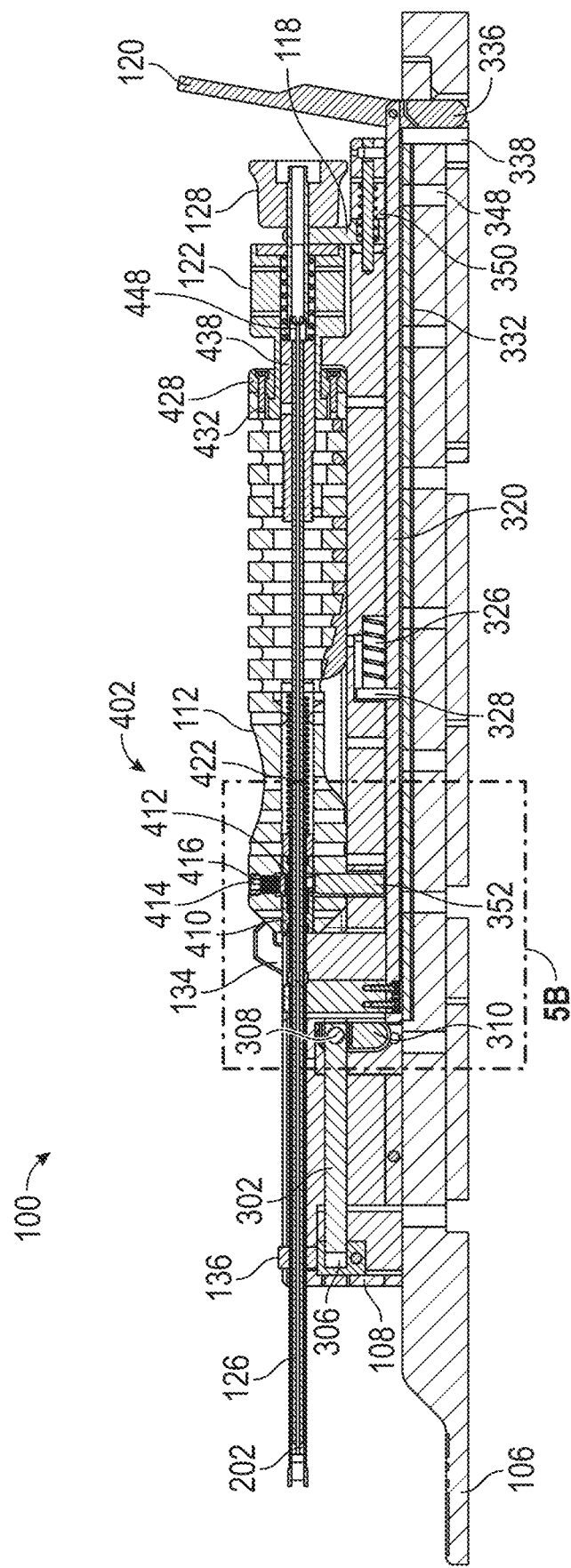
FIG. 5A shows a cross-sectional view of a system for inserting an adapter in accordance with at least one example of the present disclosure.
Figure 5B:
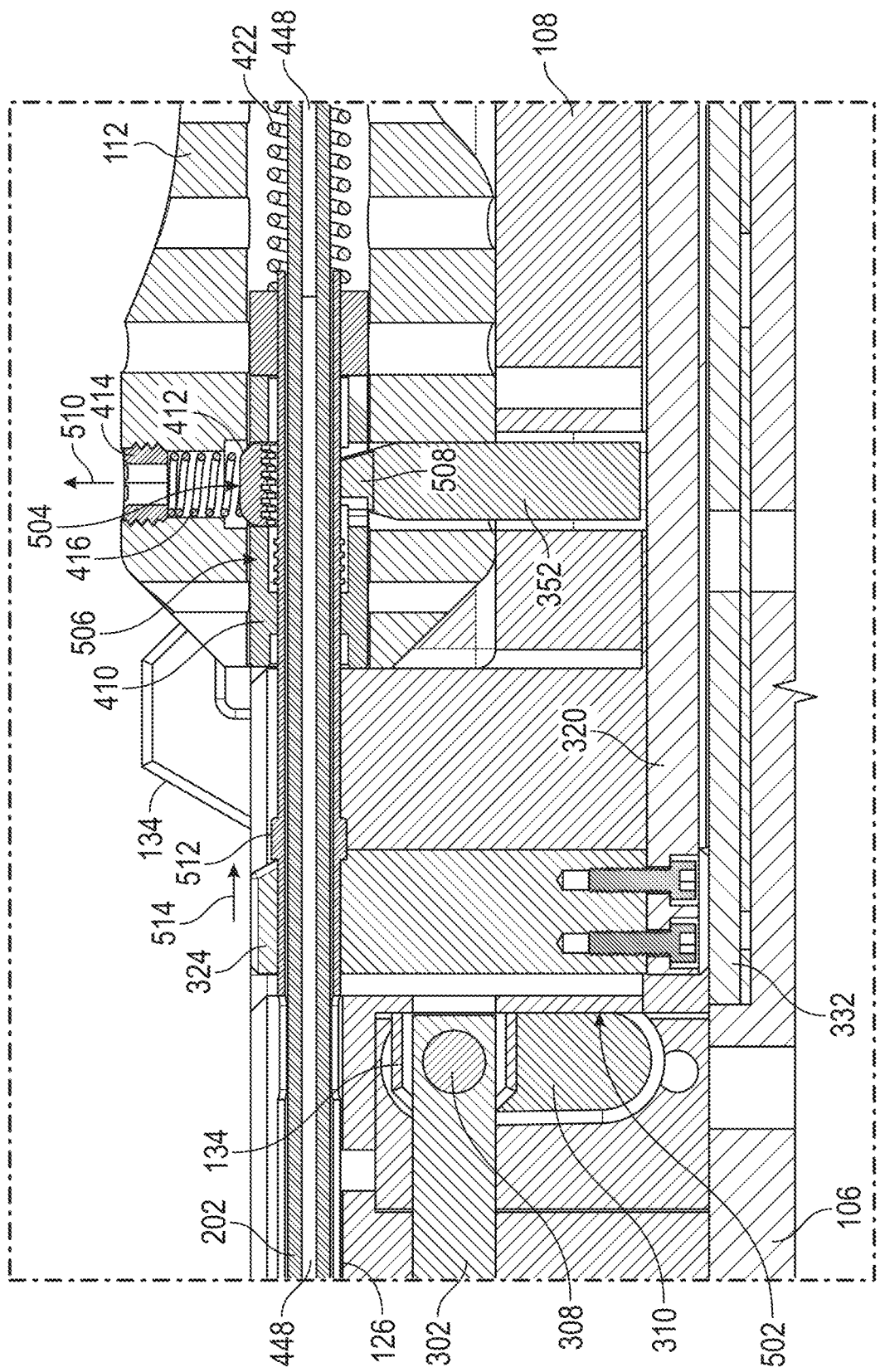
FIG. 5B shows a detail of the cross-sectional view of the system for inserting an adapter shown in FIG. 5A in accordance with at least one example of the present disclosure.

Turning now to FIGS. 5A and 5B, FIG. 5A shows a cross-sectional view of system 100. FIG. 5B shows a detail of system 100. As shown in FIG. 5B, clamp 412 can include clamp teeth 504 and engagement tube 126 can include engagement teeth 506. When adapter inserter 102 is not docked in docking station 104, spring 416 can press clamp 412 such that claim teeth 504 engage engagement teeth 506. The cooperation of claim teeth 504 with engagement teeth 506 can lock engagement tube 126 in a fixed position.

When adapter inserter 102 is docked with docking station 104, prongs 508 of lock push bar 352 can engage clamp 412. Prongs 508 can push clamp 412 in a direction indicated by arrow 510. Movement of clamp 412 away from engagement tube 126 can allow movement of engagement tube 126. For example, with clamp 412 disengaged from engagement tube 126 engagement tube pull block 324 can contact flange 512 when engagement tube pull block 324 moves in a direction as indicated by arrow 514. The contact with flange 512 and movement of engagement tube pull block 324 can cause protrusion 204 to be exposed so that adapter 132 can be coupled to engagement shaft 202.

Handle body 112, engagement tube 126, as well as the other components of adapter inserter 102 can be manufactured from metals, polymers, ceramics, or any combination thereof. In addition, the various components of adapter inserter 102 can be manufactured using injection molding, machining of billet materials, stamping, forge, etc. The selection of the materials as well as the method used to manufacture each part can be determined using a variety of factors such as wearability, ease of manufacturing, and interaction with other parts.

Figure 6:
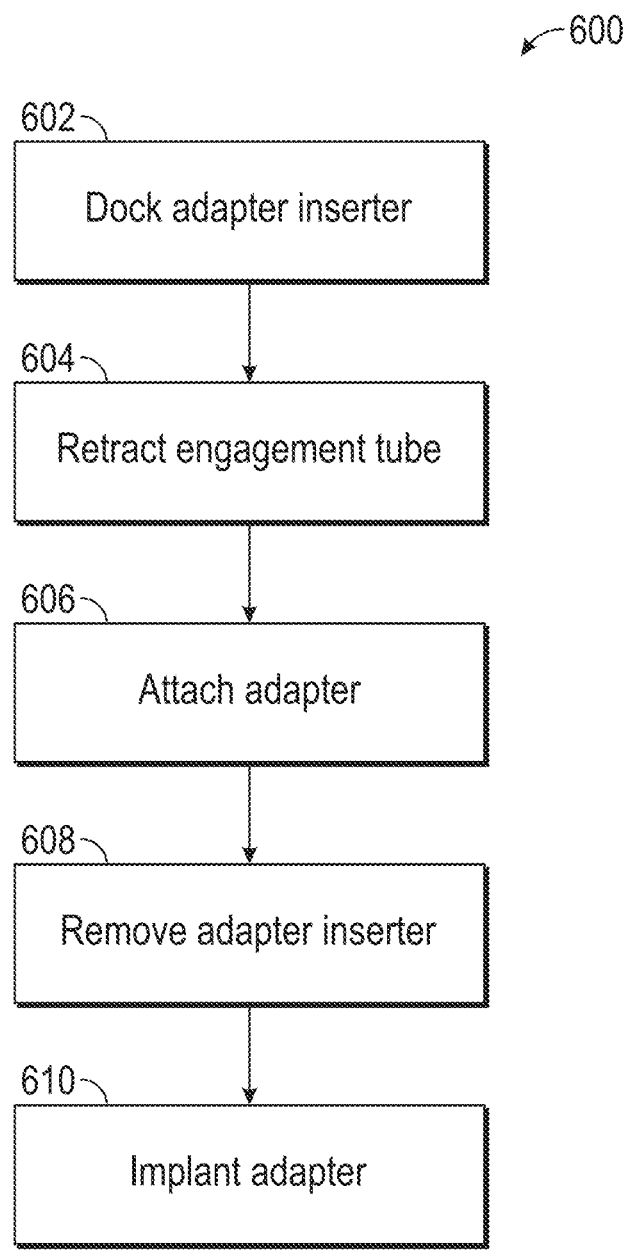
FIG. 6 shows a method in accordance with at least one example of the present disclosure.

FIG. 6 shows a method 600 for implanting an adapter, such as adapter 132, in accordance with at least one example of the present disclosure. Method 600 can begin at stage 602 where an adapter inserter, such as adapter inserter 102, can be docked to a docking station, such as docking station 104. As disclosed herein, docking an adapter inserter to a docking station can include manipulating a handle retainer push handle so as to cause handle retainers to translate so that protrusions of a handle body can be positioned within a handle block of the docking station. The handle body itself can also be positioned in a recess defined by the handle block.

Docking the adapter inserter with the docking station can also include causing a lock push block of the docking station to engage a clamp of the adapter inserter. When the lock push block engages the clamp, the clamp can disengage an engagement tube so that the engagement tube is free to be retracted.

From stage 602 method 600 can proceed to stage 604 where the engagement tube can be retracted. As disclosed herein, retracting the engagement tube can be achieved by manipulating a knob push handle. The knob push handle can be connected to a linkage shaft that can be connected to an engagement tube pull block. The engagement tube pull block can engage the engagement tube when the engagement tube pull block moves. As a result, manipulation of the knob push handle can cause the engagement tube to be retracted.

From stage 604 method 600 can proceed to stage 606 where the adapter can be attached to the adapter inserter. For example, an engagement shaft that was exposed by retraction of the engagement tube in stage 604. The adapter can be attached to the engagement shaft as disclosed herein.

From stage 606 method 600 can proceed to stage 608 where the adapter inserter can be removed from the docking station. As disclosed herein, removing the adapter inserter from the docking station can include manipulating the handle retainer push handle so as to cause handle retainers to translate as described above with respect to stage 602. Upon manipulating the handle retainer push handle, the adapter inserter can be removed from the recess defined by the handle block.

From stage 608 method 600 can proceed to stage 610 where the adapter can be implanted into a patient. As disclosed herein, implanting the adapter into the patient can include rotating a rotatable knob of the adapter inserter. Rotation of the rotatable knob can cause an inner shaft of the adapter inserter to rotate, which in turn can cause the adapter to expand and implant within bone or another anatomical structure of the patient.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A docking station for an adapter inserter, the docking station comprising:
    a handle block having a first surface that defines a first recess sized to receive a portion of the adapter inserter and a second surface that defines a channel; and
    a push assembly comprising:
    a knob push handle,
    an engagement tube pull block configured to contact a portion of an engagement tube of the adapter inserter, and
    a linkage shaft connecting the knob push handle to the engagement tube block,
    the linkage shaft slidably located in the channel, the engagement tube pull block extending upwardly from the linkage shaft through a portion of the handle bock such that a portion of the engagement tube pull block is located in the first recess.

2. The docking station of claim 1, further comprising:
    a first handle retainer arm located proximate a first end of the recess and extending from the handle block above the first surface of the handle block; and
    a handle retainer push handle operatively connected to the first handle retainer arm, the first handle retainer arm and the handle retainer push handle movable from a locked position to an unlocked position.

3. The docking station of claim 2, further comprising a second handle retainer arm, the first handle retainer arm and the second handle retainer arm located on opposite sides of a slot defined by the handle block.

4. The docking station of claim 2, further comprising a locking block located proximate a first end of the handle block, the locking block operatively connected to the handle retainer push handle and translatable normal to the first handle retainer arm.

5. The docking station of claim 4, further comprising a locking block shaft configured to cause the locking block to move upon movement of the handle retainer push handle.

6. The docking station of claim 2, wherein the handle retainer push handle and the first handle retainer arm are spring loaded.

7. The docking station of claim 1, further comprising a lock push block projecting into the recess and configured to disengage a clamp of the adapter inserter.

8. The docking station of claim 1, further comprising a knob push block located proximate the knob push handle, the knob push block defining an indentation sized to receive a portion of a rotatable knob of the adapter inserter.

9. The docking station of claim 1, further comprising a base plate connected to the second surface of the handle block.

10. A system for inserting an adapter, the system comprising:
    a docking station comprising:
    a handle block that defines a channel and a first recess,
    a lock push block connected to the handle block and protruding into the first recess, and
    a push assembly comprising a knob push handle, an engagement tube pull block, and a linkage connecting the knob push handle to the engagement tube pull block,
    the linkage slidably located in the channel, the engagement tube pull block extending upwardly from the linkage through a portion of the handle bock into the recess; and an adapter inserter comprising:
a handle body having a first end and a second end, the handle body sized to fit in a first recess defined by the handle block and defining a through hole extending from the first end to the second end,
an engagement assembly extending from the second end of the handle body and configured to engage the adapter at a tip of the engagement assembly, and
a clamp located within and proximate the second end of the handle body, the clamp arranged to engage a portion of the engagement assembly, the clamp having a contact surface arranged to engage the lock push block of the docking station.

11. The system of claim 10, wherein the engagement assembly comprises:
an engagement tube extending from the second end of the handle body; and
an engagement shaft located within the engagement tube and extending from the second end of the handle body, wherein the clamp is arranged to contact the engagement tube.

12. The system of claim 11, wherein the clamp comprises clamp teeth and the engagement tube comprises engagement teeth, the clamp teeth arranged to engage the engagement teeth.

13. The system of claim 10, wherein
the docking station further comprises:
a handle retainer arm located proximate a first end of the first recess and extending from the handle block, and
a handle retainer push handle operatively connected to the handle retainer arm, the handle retainer arm and the handle retainer push handle movable from a locked position to an unlocked position; and
the adapter inserter further comprises:
at least one protrusion extending from the handle body and located proximate the second end of the handle body, the at least one protrusion sized to engage the first handle retainer of the docking station.

14. The system of claim 13, further comprising a second handle retainer arm, the handle retainer arm and the second handle retainer arm located on opposite sides of a slot defined by the handle block.

15. The system of claim 14, wherein the lock push block is operatively connected to the handle retainer push handle and translatable normal to the handle retainer arm.

16. The system of claim 15, further comprising a locking block shaft configured to cause the lock push block to move upon movement of the handle retainer push handle.

17. The system of claim 14, wherein the handle retainer push handle and the handle retainer arm are spring loaded.

18. The system of claim 10, further comprising a base plate connected to a second surface of the handle block.

19. The system of claim 10, further comprising a knob push block located proximate the knob push handle, the knob push block defining an indentation sized to receive a portion of a rotatable knob of the adapter inserter.

* * * * *